United States Patent [19]

Canfield et al.

[11] Patent Number: 4,808,598

[45] Date of Patent: Feb. 28, 1989

[54] METHOD FOR INDUCING PROTECTION IN AN ANIMAL AGAINST CYANIDE POISONING USING 8-AMINOQUINOLINES

[75] Inventors: Craig J. Canfield, Upper Marlboro; Melvin H. Heiffer, Bethesda, both of Md.; Don W. Korte, Jr., San Francisco, Calif.

[73] Assignee: The United States of America as represented by the Secretary of the Army, Washington, D.C.

[21] Appl. No.: 880,476

[22] Filed: Jun. 30, 1986

[51] Int. Cl.$^4$ .................... A61K 31/47; C07D 215/40
[52] U.S. Cl. .................... 514/312; 546/153; 546/159; 514/313
[58] Field of Search ............ 514/313, 312; 546/153, 546/159

[56] References Cited

U.S. PATENT DOCUMENTS

| | | | |
|---|---|---|---|
| 2,719,848 | 10/1955 | Geschickter et al. | 546/153 X |
| 3,798,322 | 3/1974 | Manning | 514/313 |
| 4,209,519 | 3/1978 | Kinnamon | 514/313 |
| 4,302,459 | 11/1981 | Steck et al. | 514/313 |

Primary Examiner—Floyd D. Higel
Attorney, Agent, or Firm—Anthony T. Lane; William V. Adams; Werten F. W. Bellamy

[57] ABSTRACT

This invention is directed to a method for inducing protection in an animal against poisoning resulting from exposure to toxic levels of cyanide comprising orally administering to said animal a therapeutically effective amount of a compound having the formula:

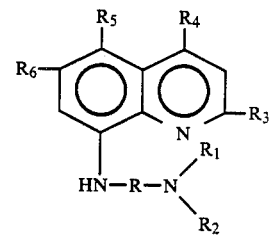

wherein R represents

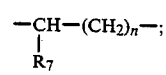

$R_1$ and $R_2$ represent hydrogen, methyl or ethyl; $R_3$ represent hydrogen, alkyl having 1 to 4 represents hydrogen, alkyl having 1 to 4 carbon atoms or alkoxy having 1 to 4 carbon atoms; $R_4$ represents hydrogen or alkyl having 1 to 4 carbon atom; $R_5$ represents hydrogen, alkyl having 1 to 7 carbon atoms, alkoxy having 1 to 7 carbon atoms, phenyl phenoxy, or substituted phenyl or phenoxy groups having the formula

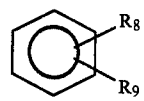

$R_6$ represents hydrogen, alkyl having 1 to 4 carbon atoms, or alkoxy having 1 to 4 carbon atoms; $R_7$ represents hydrogen, methyl or ethyl; $R_8$ and $R_9$ represent chloro, bromo, fluoro, trifluoromethyl or methoxy groups; n represents the integers 3,4,5,6 and 7; or pharmaceutically acceptable salts thereof wherein the salt forming acid or acid-hydrate is selected from the group consisting essentially of hydrochloric acid, phosphoric acid, nitric acid, sulfamic acid, sulfuric acid, maleic acid, fumaric acid, citric acid, beta-resorcylic acid and hydrobromic acid.

13 Claims, No Drawings

METHOD FOR INDUCING PROTECTION IN AN ANIMAL AGAINST CYANIDE POISONING USING 8-AMINOQUINOLINES

BACKGROUND OF THE INVENTION

1. Field of the Invention

This invention relates to chemical inducement of low levels of methemoglobin in animals to provide protection against anticipated exposure to toxic levels of cyanide, through the oral administration of an 8-aminoquinoline derivative.

2. Prior Disclosure

All publications or patents mentioned in this specification are herein incorporated by reference.

As early as the 1930's, a pharmacological method of inducing methemoglobin production for treatment of cyanide intoxication was discovered. This method was designed for immediate treatment of a victim displaying symptoms of acute cyanide poisoning. The pharmacological principle of the treatment was to oxidize 30–40 percent of the blood hemoglobin to be methemoglobin in the poisoned victim in order to sequester an unknown body level of cyanide. Such levels of methemoglobin are above the threshold of methemoglobin toxicity and would be intolerable to normal, healthy, and active humans or animals.

A major problem with this treatment is that a victim exposed to toxic levels of cyanide has very little time to receive life saving treatment. Also, if exposure to cyanide is in the gaseous form, it is likely that nearby persons will be similarly exposed and rendered incapable of providing treatment. Therefore, the victim will often be faced with giving himself an injection of the antidote while undergoing the agony of cyanide poisoning.

SUMMARY OF THE INVENTION

This invention relates to novel means for inducing the production of blood methemoglobin in animals, at sufficient levels to afford post- or pretreatment of said animals against poisoning resulting from exposure to toxic levels of cyanide. It is based upon the use or administration of therapeutically effective amounts of certain 8-aminoquinoline compositions which are administered orally.

The present invention avoids many problems associated with previously known treatments by orally administering a compound to induce constant, ongoing levels of methemoglobin sufficient to provide protection to animals, against exposure to toxic levels of cyanide. For persons likely to be exposed to cyanide, this is a preventive measure rather than a post-exposure method of treatment.

DETAILED DESCRIPTION OF THE INVENTION

Practical utility has been established for 8-aminoquinoline compositions having the formula:

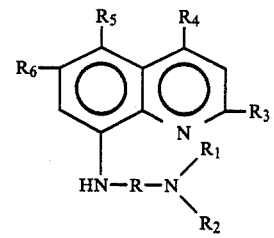

wherein R represents

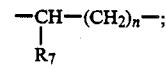

$R_1$ and $R_2$ represent hydrogen, methyl or ethyl; $R_3$ represents hydrogen, alkyl having 1 to 4 carbon atoms or alkoxy having 1 to 4 carbon atoms; $R_4$ represents hydrogen or alkyl having 1 to 4 carbon atoms; $R_5$ represents hydrogen, alkyl having 1 to 7 carbon atoms, alkoxy having 1 to 7 carbon atoms, phenyl, phenoxy, or substituted phenyl or phenoxy groups having the formula

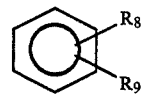

$R_6$ represents hydrogen, alkyl having 1 to 4 carbon atoms, or alkoxy having 1 to 4 carbon atoms; $R_7$ represents hydrogen, methyl or ethyl; $R_8$ and $R_9$ represent chloro, bromo, fluoro, trifluoromethyl or methoxy groups; n represents the integers 3, 4, 5, 6 and 7; and pharmaceutically acceptable salts thereof wherein the salt forming acid or acid-hydrate is selected from the group consisting essentially of hydrochloric acid, phosphoric acid, nitric acid, sulfamic acid, sulfuric acid, maleic acid, fumaric acid, citric acid, beta-resorcylic acid and hydrobromic acid. A representative composition which has found to be especially useful is 8-(6-diethylaminohexylamino)-6-methoxy-4-methylquinoline dihydrochloride which is represented by the formula:

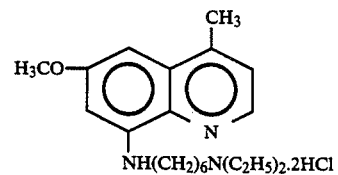

We have discovered that when the 8-aminoquinoline compositions are administered at a dosage level of from about 2 to 5 mg/kg body weight of the animal, they induce the production of blood methemoglobin in said animal thereby providing effective treatment against poisoning from exposure to toxic levels of cyanide. Although the compositions used in this invention are effective for therapy (post treatment) and prophylaxis (pretreatment), we have found, for example, that the use of a suitable 8-aminoquinoline composition at a dosage level sufficient to raise the blood methemoglobin in the animal to within the range of about 10 to about 12 percent provides complete prophylactic protection to said animal against exposure to dosage levels of potassium cyanide within the range of about 1.85 to 5.5 mg/kg body weight (BW).

EXAMPLE

The working example setforth below illustrates the use of representative compositions, but in no way limit the scope of this invention.

Some of the compounds of the present invention are described as an anti-leishmanial for use in treating animals infected with leishmania. U.S. Pat. No. 4,209,519 (Kinnamon) discloses the use of the compound as as an anti-leishmanial agents. It recommends significantly higher dosages than the present invention and it demonstrates activity as an anti-leishmanial agent in certain animals. The tested dosage levels of these anti-leishmanial agents were 208, 52 and 13 mg/kg body weight per day. However, in the present invention, the recommended dosage for the pre- or post-treatment of cyanide poisoning is within the range of 2 to 5 mg/kg, most preferably, 2 to 3 mg/kg body weight per day. These dosages are substantially smaller for the induction of methemoglobin because dosages on the same order as those prescribed in the Kinnamon patent would produce intolerable levels of methemoglobin. Therefore, the present invention is clearly distinguishable from the Kinnamon patent with respect to the purpose for which the drug is used, dosages of the drug administered, and resultant pharmacological effects of the drug. The U.S. Pat. Nos. 2,719,848 (Geschickter, et al.) and 4,302,459 (Steck, et al.) relate solely to the use of 8-aminoquinoline compounds for treatment of alergic disorders and leihmanial (i.e. asthma), respectively.

The present invention has several advantages over prior methods for dealing with exposure to toxic levels of cyanide. The compound is easy to administer orally. Additionally, the protection provided prior to exposure substantially reduces the likelihood of harm by unsuspected exposure, and is long acting. The protective level of methemoglobin is readily induced and sustained over effective periods of time without causing harmful side effects which would be medically unacceptable. This method of treatment is efficacious even upon repeated exposure so long as the drug is taken at the prescribed intervals.

When administered in oral dosage form, the 8-aminoquinoline derivative may be incorporated into single layer tablets, multi-layer tablets, coated tablets, uncoated tablets, capsules, dragees, and other formulations. Such oral dosage forms may include optional, non-interfering pharmaceutical carriers or adjuvants such as corn starh, talc, lactose or other substances which are known by those skilled in the art.

DESCRIPTION OF PREFERRED EMBODIMENT

The synthesis of 8-(6-Diethylaminohexylamino)-6-methoxy-4-methylquinoline dihydrochloride (hereinafter called DMMD) and related compositions are described in detail in *J. Am. Chem. Soc.*, Vol. 68, pages 1556-1559, 1946.

Assessment of the effectiveness of the present treatment was done in a model test system employing purebred beagle dogs. This test system is considered by medical scientists to be conclusive as to the efficacy in humans because of the high degree of similarity between the kinetics of the dog's red blood cell reductase enzymes and those of man.

Sixteen male (M) and eleven female (F) purebred beagle dogs approximately 9 to 12 months of age, were used in this experiment. All dogs were examined upon receipt by a veterinarian who, where appropriate, issued a certificate of health for all dogs used in the experiment. The animals received daily portions of approximately 400 grams/dog of pelleted Purina Canine Diet #5006 ad libitum. Food was presented to each animal (dog) for approximately two hours daily.

In preparation for the initiation of the experiment, the animals were divided into six groups and administered DMMD and potassium cyanide (KCN) as follows:

TABLE NO. 1

| Group | No. of M | No. of F | Level of DMMD (mg/kg) | Level of KCN |
|---|---|---|---|---|
| A | 3 | 2 | 4.83 | $LD_{50}$ (A) |
| B | 3 | 2 | 4.83 | $2 \times LD_{50}$ |
| C | 3 | 2 | 4.83 | $3 \times LD_{50}$ |
| D | 3 | 2 | 4.83 | $4 \times LD_{50}$ |
| E | 1 | 1 | None | $2 \times LD_{50}$ |
| F | 3 | 2 | 4.83 | $3.5 \times LD_{50}$ |

(A) $LD_{50}$ is the dose at which 50% of untreated beagles died from KCN exposure.

Each animal was identified by an ear tattoo number and a cage card containing the project number and the ear tattoo number.

DMMD was administered in salt form via a capsule at a dose of 4.83 mg/kg body weight. Capsules (size II and No. 0) containing 1, 30, 35, 40, 45 or 50 mg of DMMD were prepared at Food and Drug Research Laboratories (FDRL), while 5 mg capsules were provided by us. Dosing was done to the nearest mg. All capsules were protected from the light prior to dosing. Each dog in groups A, B, C, D, and F was dosed with DMMD once daily for at least four consecutive days. Animals in group E served as controls and received no DMMD. No DMMD was administered after the KCN was given to the animals.

A lethal dose of potassium cyanide ($LD_{50}$, $2 \times LD_{50}$, $3 \times LD_{50}$, $3.5 \times LDS_{50}$, $4 \times LD_{50}$) was administered to each dog when the blood methemoglobin level induced by DMMD had decreased to approximately 10–12% after peak levels had been attained (see Todd, Sanford and Davidsohn, *Clinical Diagnosis and Management*, 16th edition, pages 511–512 and 869–870 (1979) for procedures regarding determination of blood methemoglobin levels). Each concentration of the potassium cyanide solution was prepared by dissolving an appropriate amount of KCN in an appropriate volume of physiological (0.85% NaCl) saline. The concentration of each KCN solution was checked prior to dosing by use of a titrimetric method (American Public Health Association, 1980). Analyses showed that in all cases solutions were mixed to within ±0.05 mg/ml of the theoretical value. Each solution of KCN was administered at a constant volume (1.0 ml/kg body weight). Each animal was suspended in a sling and the cephalic vein of one forelimb was cannulated using a L-CATH-™ IV Cath Placement Set (catheter—23GA, 2.4 in; needle—20GA; Luther Medical Products Inc., Costa Mesa, CA 92626; catalog No. 23P6). A single dose of KCN solution was administered intravenously via the cephalic vein over a period of one minute. Animals in group E (control) were administered cyanide at a concentration of $2 \times LD_{50}$ the first day on which the first group D animal was treated with cyanide.

Animals were observed for mortality and signs of toxicity frequently during the days of dosing (DMMD and cyanide) and twice daily thereafter for three days following cyanide administration. For the animals which died following cyanide injection, death was ascertained with the use of a stethoscope to determine cessation of heart beat. A summary of dosing (DMMD and KCN) and mortality data is given in Table 2.

TABLE NO. 2

Summary of Dosing and Mortality Data

| Group | Animal and Sex | Level of DMMD (mg/kg BW) | Level of KCN[c] | % Methemoglobin at KCN Dosing | Fate[a] |
|---|---|---|---|---|---|
| A | 2UT2 M | 4.83 | $LD_{50}$ | 10.79 | S |
|   | 2ST1 M | 4.83 | $LD_{50}$ | 12.32 | S |
|   | CMK1 M | 4.83 | $LD_{50}$ | 10.71 | S |
|   | CBP1 F | 4.83 | $LD_{50}$ | 11.41 | S |
|   | 2TW5 F | 4.83 | $LD_{50}$ | 12.36 | S |
| B | 2TY5 M | 4.83 | $2 \times LD_{50}$ | 9.53 | S |
|   | CCJ1 M | 4.83 | $2 \times LD_{50}$ | 12.15 | S |
|   | CBT2 M | 4.83 | $2 \times LD_{50}$ | 11.25 | S |
|   | 2ZF3 F | 4.83 | $2 \times LD_{50}$ | 12.22 | S |
|   | 2YT5 F | 4.83 | $2 \times LD_{50}$ | 11.14 | S |
| C | CAQ4 M | 4.83 | $3 \times LD_{50}$ | 11.94 | S |
|   | 2XS3 M | 4.83 | $3 \times LD_{50}$ | 11.59 | S |
|   | 2XS2 M | 4.83 | $3 \times LD_{50}$ | 11.82 | S |
|   | 2ZR4 F | 4.83 | $3 \times LD_{50}$ | 10.34 | S |
|   | 2ZM5 F | 4.83 | $3 \times LD_{50}$ | 11.57 | S |
| D | 3AFX3 M | 4.83 | $4 \times LD_{50}$ | 11.33 | D |
|   | 3AEV1 M | 4.83 | $4 \times LD_{50}$ | 9.63 | D |
|   | 3AFQ1 M | 4.83 | $4 \times LD_{50}$ | 12.19 | D |
|   | 3ADS4 F | 4.83 | $4 \times LD_{50}$ | 10.95 | D |
|   | 3ABZ5 F | 4.83 | $4 \times LD_{50}$ | 12.29 | D |
| E | CCJ5 M | 0 | $2 \times LD_{50}$ | 0.98 | D |
|   | 2SM6 F | 0 | $2 \times LD_{50}$ | 0.98 | D |
| F | 3AD03 M | 4.83 | [b] | — | — |
|   | 3AFS4 M | 4.83 | $3.5 \times LD_{50}$ | 10.92 | S |
|   | 3ACU2 M | 4.83 | $3.5 \times LD_{50}$ | 11.61 | D |
|   | 2CR4 F | 4.83 | $3.5 \times LD_{50}$ | 11.01 | S |
|   | CAN5 F | 4.83 | $3.5 \times LD_{50}$ | 11.65 | D |

[a] S = Survived; D = Died.
[b] Animal not administered KCN due to low blood methemoglobin level.
[c] $LD_{50}$ = 1.85 mg/kg; $2 \times LD_{50}$ = 3.70 mg/kg; $3 \times LD_{50}$ = 5.5 mg/kg; $3.5 \times LD_{50}$ = 6.48 mg/kg and $4 \times LD_{50}$ = 7.40 mg/kg.

All animals treated in accordance with this invention and injected with cyanide at a level of $LD_{50}$, $2 \times LD_{50}$ or $3 \times LD_{50}$ survived the challenge, while the five animals injected with cyanide at a level of $4 \times LD_{50}$ died following the injection. For the four animals treated in accordance with this invention and injected with cyanide at a level of $3.5 \times LD_{50}$, two died following KCN administration, while two animals survived the KCN challenge. Both animals in the control group (E) died following $2 \times LD_{50}$ KCN administration.

The calculated dose at which 50% of the animals given KCN showed an effect, following a single intravenous injection in beagle dogs that had pre-existing blood methemoglobin levels of 10–12% (induced by administration of DMMD) was 6.48 mg/kg body weight. This value was 3.5 times greater than the $LD_{50}$ value obtained with a single injection of KCN in dogs with non-induced ("normal") blood methemoglobin levels. Thus, a "protective index" of 3.5 was established for an induced 10–12% methemoglobin level.

Dosages for other animals are readily determinable by extrapolating the dosage of the Beagle and monitoring of the blood methemoglobin level during DMMD administration. This dosage is appropriate for preventive protection against cyanide poisoning.

In the expected scenario the dosages mentioned above will suffice to protect animals exposed to cyanide. This protection will last for 10 or 11 days on the average. However, if the need should arise, protection for a longer period of time is possible. One dosage in the aforestated amounts each week will maintain the desired methemoglobin level in the body. This will afford long-term protection if it is deemed necessary.

Also, this invention is not to be limited to protection by inducing methemoglobin levels in the range of 10–12%. The induction of lower levels down to 1 to 2% is contemplated and may, in fact be desirable for certain situations. This can be accomplished within the scope of this invention by simply reducing the dosage levels of the 8-aminoquinoline, such as, DMMD by an appropriate amount.

A rough calculation of the necessary methemoglobin level can be made by estimating the approximate number of cyanide molecules that need to be sequestered, computing the number of methemoglobin molecules needed to sequester the cyanide, calculating the percentage of hemoglobin this represents from the average number of hemoglobin molecules present in the animal's body, and adding 4–5% to compensate for the time it will take the methemoglobin to come into contact with the cyanide in the body. This last factor is necessary because the cyanide will cause harmful effects while traveling through the body if it is not sequestered quickly and efficiently. Therefore, it is necessary to have an excess of methemoglobin to ensure quick and efficient neutralization of the cyanide.

This invention also contemplates inducing higher levels of blood methemoglobin in the body, for a short period of time, if the need should arise. However, levels substantially above 10–12% will normally produce some side effects if maintained for the necessary period. The 10–12% level is, therefore, preferred because it maximizes cyanide protection while minimizing harmful side effects.

We claim:

1. A method for inducing protection in an animal against poisoning resulting from exposure to toxic levels of cyanide comprising orally administering to said animal a therapeutically effective amount of a compound having the formula:

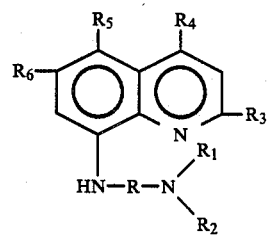

wherein R represents

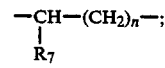

$R_1$ and $R_2$ represent hydrogen, methyl or ethyl; $R_3$ represents hydrogen, alkyl having 1 to 4 carbon atoms or alkoxy having 1 to 4 carbon atoms; $R_4$ represents hydrogen or alkyl having 1 to 4 carbon atoms; $R_5$ represents hydrogen, alkyl having 1 to 7 carbon atoms, alkoxy having 1 to 7 carbon atoms, phenyl, phenoxy, or substituted phenyl or phenoxy groups having the formula

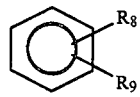

$R_6$ represents hydrogen, alkyl having 1 to 4 carbon atoms, or alkoxy having 1 to 4 carbon atoms; $R_7$ represents hydrogen, methyl or ethyl; $R_8$ and $R_9$ represent chloro, bromo, fluoro, trifluoromethyl or methoxy groups; n represents the integers 3, 4, 5, 6 and 7; or pharmaceutically acceptable salts thereof wherein the salt forming acid or acid-hydrate is selected from the group consisting essentially of hydrochloric acid, phosphoric acid, nitric acid, sulfamic acid, sulfuric acid, maleic acid, fumaric acid, citric acid, beta-resorcylic acid and hydrobromic acid.

2. The method according to claim 1 wherein $R_1$ and $R_2$ are alkyl groups containing 1 to 7 carbon atoms.

3. The method according to claim 2 wherein $R_7$ is hydrogen.

4. The method according to claim 2 wherein $R_7$ is hydrogen or methyl and n is 3.

5. The method according to claim 2 wherein $R_7$ is hydrogen, $R_1$ and $R_2$ are hydrogen or isopropyl.

6. The method according to claim 3 wherein $R_1$ and $R_2$ are ethyl.

7. The method according to claim 6 wherein $R_7$ is hydrogen and n is 6.

8. The method according to claim 1 wherein said effective amount is sufficient to raise the level of blood methemoglobin to about 1 to 20%.

9. The method according to claim 8 wherein the level of blood methemoglobin is about 10 to 12%.

10. The method according to claim 1 wherein said compound is administered daily for a period of 4 to 6 days.

11. The method according to claim 1 wherein said compound is administered daily for a period of 4 to 6 days and immediately thereafter administered once per week to maintain protection against cyanide poisoning.

12. The method according to claim 1 wherein the administration is effected prior to cyanide poisoning.

13. The method according to claim 1 wherein the administration is effected subsequent to cyanide poisoning.